(12) United States Patent
Georgeson et al.

(10) Patent No.: US 7,898,246 B2
(45) Date of Patent: Mar. 1, 2011

(54) METHOD AND APPARATUS FOR NONDESTRUCTIVE INSPECTION OF INTERWOVEN WIRE FABRICS

(75) Inventors: Gary E. Georgeson, Federal Way, WA (US); James H. Lee, Ravensdale, WA (US)

(73) Assignee: The Boeing Company, Chicago, IL (US)

( * ) Notice: Subject to any disclaimer, the term of this patent is extended or adjusted under 35 U.S.C. 154(b) by 881 days.

(21) Appl. No.: 11/832,428

(22) Filed: Aug. 1, 2007

(65) Prior Publication Data
US 2009/0033323 A1    Feb. 5, 2009

(51) Int. Cl.
*G01B 7/26* (2006.01)
(52) U.S. Cl. .................................... 324/229; 324/237
(58) Field of Classification Search .............. 324/229, 324/237
See application file for complete search history.

(56) References Cited

U.S. PATENT DOCUMENTS 4,924,182 A    5/1990    Vernon et al.
5,717,332 A    2/1998    Hedengren et al.

FOREIGN PATENT DOCUMENTS

| EP | 1657545 | 5/2006 |
| EP | 1783501 | 5/2007 |
| WO | 8700288 | 1/1987 |

OTHER PUBLICATIONS

Siegel, "Automation for Non-Destructive Inspection of Aircraft" Proceedings of Conference on Intelligent Robotics in Field, Factory, Service and Space, Jan. 1994, pp. 1-11.

*Primary Examiner*—Reena Aurora
(74) *Attorney, Agent, or Firm*—Yee & Associates, P.C.; Dennis R. Plank (57) ABSTRACT

A method and apparatus for nondestructive inspection of interwoven wire fabric components. The apparatus comprises a probe, a power source, and a display system. The probe is capable of creating a magnetic field for a plurality of wires in an interwoven wire fabric component such that disturbances of the magnetic field caused by the plurality of wires can be detected. The power is a source connected to the probe and is capable of sending an alternating current through the probe to generate the magnetic field for the wire. The display system is connected to the probe and is capable of displaying results from detecting the magnetic field and disturbances of the magnetic field.

17 Claims, 5 Drawing Sheets

METHOD AND APPARATUS FOR NONDESTRUCTIVE INSPECTION OF INTERWOVEN WIRE FABRICS

BACKGROUND INFORMATION

1. Field

The present disclosure relates generally to inspecting components and in particular to a method and apparatus for identifying variations in a component. Still more particularly, the present disclosure relates to a method and apparatus for nondestructive inspection of interwoven wire fabrics.

2. Background

Today's aircraft are being designed and built with greater percentages of composite materials. In some aircraft, up to fifty percent of the structural components are being manufactured with composite materials. Composite materials are tough, light-weight materials. These types of materials may be made by combining two or more dissimilar products, such as fibers and resins, to create a product with improved or exceptional structural properties not present in the original materials.

Composite materials are used in aircraft to meet goals, such as reducing weight and increasing payloads in the aircraft. Further, composite materials also are used because these types of materials have improved fatigue, life, and increased corrosion resistance as compared to other currently used materials.

Although composite materials are lighter and have better mechanical and fatigue properties as compared to aluminum, these types of materials are less electrically conductive and have poor electromagnetic shielding. These features cause poor current dissipation when an electromagnetic effect, such as a lightning strike occurs. Further, composite materials are subject to greater damage due to lightning strikes than traditional aluminum materials used in aircraft.

Specifically, when lightning hits an aircraft, a conductive path on the skin of the aircraft allows the electricity to travel along the skin and exit at some other location on the aircraft. Without an adequate conductive path, arcing and hot spots can occur. These types of effects may char, delaminate, and/or penetrate the skin of the aircraft. As a result, the load bearing characteristics of the structure of the aircraft may be returned. Thus, the lower electrical shielding capability of composite materials increases the likelihood that circuits within the aircraft may be affected by the lightning strike.

One current mechanism used to protect composite skins on aircraft against lightning strike damage, is to include conductive lightning skin protection systems. These types of systems may be present either in or on the composite skins of an aircraft. One type of system used to provide a conductive path on the aircraft is an interwoven wire fabric. With this type of system, wires, such as phosphor-bronze wires are embedded in the top layer of the composite material nearest the wind swept surface. This type of material is commonly used in the fuselage of an aircraft. Other types of systems may include the use of a thin copper foil, such as on the wings of an aircraft using composite materials.

With an interwoven wire fabric system in the fuselage, the wires typically have a thickness range of about 0.003 to about 0.004 inches. Further, these types of wires are spaced apart from each other. The spacing is around one tenth of an inch in a ninety degree mesh pattern.

In inspecting installations of composite skins containing interwoven wire fabric, it is desirable to be able to have these wires not more than a selected distance below the surface of the skin. This distance between the surface and the skin is for economic reasons, and not safety reasons. With respect to economic issues, it is more expensive if the distance to the surface of the skin from the wires is too great. The economic costs are larger with the greater distance because increased damage to layers above the interwoven wire fabric may occur. For example, damage to this layer and layers such as paint may increase with lightning strikes as compared to a smaller distance from the surface of the skin to the wires.

Additionally, it is desirable to determine if bonded repairs on composite panels containing interwoven wire fabrics have a sufficient overlap between the patch material and the current material. The overlap width should be sufficient to allow the transfer of energy from a lightning strike on a bonded repair section into the parent material of the fuselage. The overlap width is the width of the edge of the patch material extends over the parent material. The width is typically about an inch. At the overlap, the repair fabric is on top of the parent material, so that the fabric is essentially doubled up in this region. This width is constant all around the patch area. In inspecting new installations and repairs, it is desirable to be able to make these types of inspections in a nondestructive manner.

SUMMARY

The different advantageous embodiments provide a method and apparatus for nondestructive inspection of interwoven wire fabric components. The apparatus comprises a probe, a power source, and a display system. The probe is capable of creating a magnetic field for a plurality of wires in an interwoven wire fabric component such that disturbances of the magnetic field caused by the plurality of wires can be detected. The power is a source connected to the probe and is capable of sending an alternating current through the probe to generate the magnetic field for the wire. The display system is connected to the probe and is capable of displaying results from detecting the magnetic field and disturbances of the magnetic field.

In one advantageous embodiment, a system for nondestructive inspection of an interwoven wire fabric component comprises a scanner arm, a probe, a scanner, and a computer. The scanner arm is connected to the scanner and is capable of being moved over the interwoven wire fabric component. The probe is connected to the scanner arm and is capable of creating a magnetic field for a plurality of wires in an interwoven wire fabric component such that disturbances of the magnetic field caused by the plurality of wires in response to the magnetic field can be detected. The scanner is capable of moving the scanner arm over the interwoven fabric component. The computer is capable of controlling the scanner to move the scanner arm and capable of receiving signals from the probe, wherein the computer generates results from the signals and presents the results on a display in the data processing system.

In another advantageous embodiment, a method for nondestructive inspection of an interwoven wire fabric component is present. An alternating current at a frequency is sent though a probe coil having a number of coils, a diameter for the number of coils, and a diameter for a wire in the number of coils to generate a first magnetic field that generates a response in a selected number of wires in the interwoven wire fabric component. The probe coil is positioned in a location relative to the interwoven wire fabric component to cause the selected number of wires in the interwoven wire fabric component to generate a second magnetic field. Changes in the first magnetic field in response to the second magnetic field are detected.

The features, functions, and advantages can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the invention are set forth in the appended claims. The invention itself, however, as well as a preferred mode of use, further objectives and advantages thereof, will best be understood by reference to the following detailed description of an advantageous embodiment of the present disclosure when read in conjunction with the accompanying drawings, wherein:

DETAILED DESCRIPTION

Figure 1:
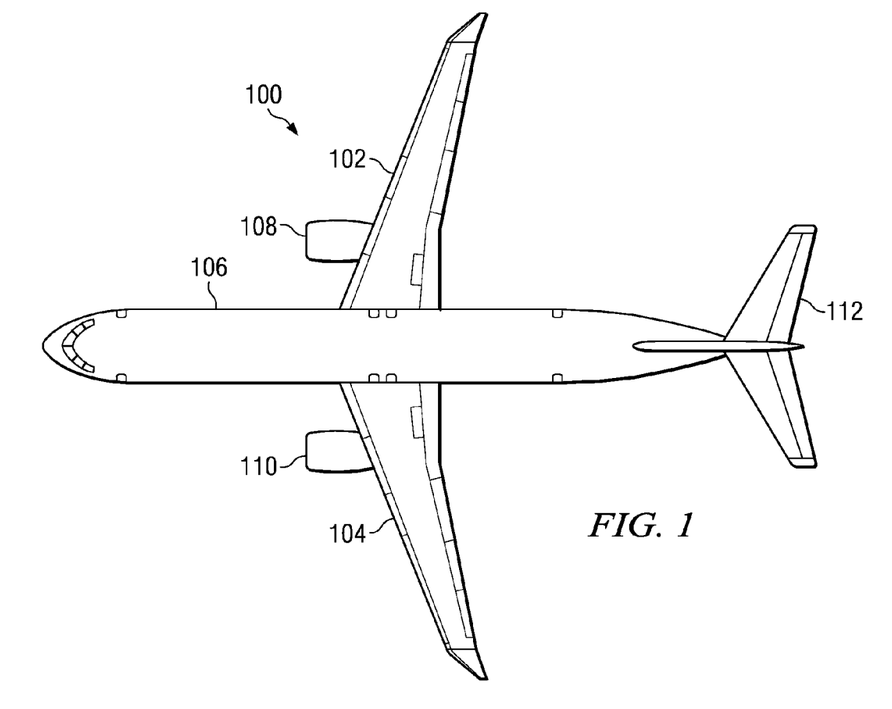
FIG. 1 is a diagram of an aircraft in which an advantageous embodiment may be implemented.

With reference now to the figures, and in particular with reference to FIG. 1, a diagram of an aircraft is depicted in which an advantageous embodiment may be implemented. Aircraft 100 is an example of an aircraft in which nondestructive inspection of interwoven wire fabric components may be implemented. In this illustrative example, aircraft 100 has wings 102 and 104 attached to fuselage 106. Aircraft 100 includes wing mounted engine 108, wing mounted engine 110, and tail 112.

The different advantageous embodiments may be implemented to perform nondestructive inspections of interwoven wire fabric components found in portions of aircraft 100, such as fuselage 106. One or more of the different advantageous embodiments may be used to inspect repairs to interwoven wire fabric components, as well as new installations of these types of components.

Figure 2:
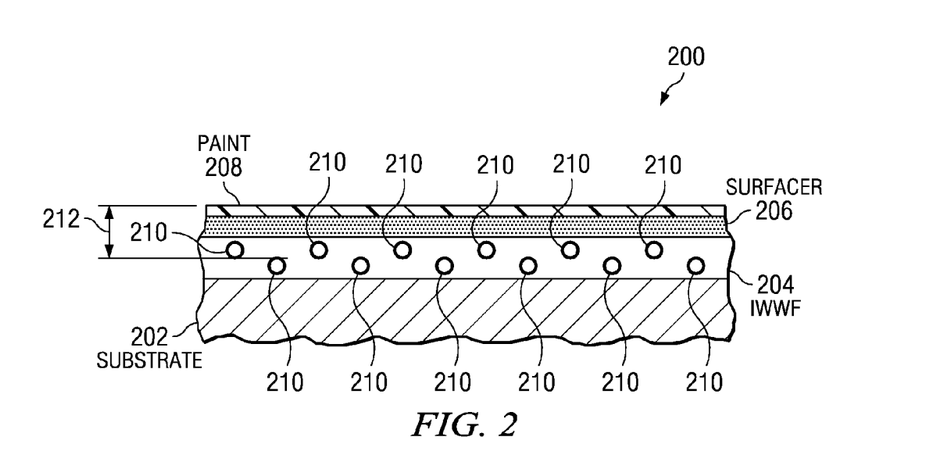
FIG. 2 is a diagram illustrating a cross-section of an aircraft skin including interwoven wire fabric wires in accordance with an advantageous embodiment.

Turning now to FIG. 2, a diagram illustrating a cross-section of an aircraft skin including interwoven wire fabric wires is depicted in accordance with an advantageous embodiment. In this example, section 200 is a cross-section of a skin on a portion of aircraft 100 in FIG. 1. In particular, section 200 is a cross-section from the skin of fuselage 106 in FIG. 1. In this example, section 200 includes substrate layer 202, interwoven wire fabric layer (IWWF) 204, surfacer layer 206, and paint layer 208. In these examples, the different layers in section 200 are part of the interwoven wire fabric component.

An interwoven wire fabric component is a component from which measurements, such as wire depths or overlapping between wires, are desired. Depending on the implementation, the interwoven wire fabric component may only include interwoven wire fabric layer 204, surfacer layer 206, and paint layer 208. Of course, the interwoven wire fabric component may include other layers in addition to or in place of the ones illustrated in these examples.

Substrate layer 202 is a composite substrate for the skin of a fuselage in this example. Interwoven wire fabric layer 204 contains wires 210, which provide a conductive path for electromagnetic effects, such as a lightning strike. Surfacer layer 206 provides a coating or surface for the application of paint layer 208.

Section 200 is an example of a section of a component in which a nondestructive inspection of interwoven wire fabric layer 204 may be made. In these examples, a distance, such as distance 212, is measured to identify a thickness of the dielectric above wires 210 within interwoven wire fabric layer 204. In these examples, the dielectric includes surfacer layer 206 and paint layer 208. The dielectric may include other materials or layers, such as a sealant, a nonconductive primer, or some other combination of those materials along with surfacer layer 206 and paint layer 208.

The thickness of the dielectric layer above wires 210 is important because the thickness impacts the dissipation of electrical energy from lightning strikes. As distance 212 increases, greater damage may occur when lightning strikes are encountered. This type of damage is an economic issue rather than a safety issue. The damage caused by lighting strikes is to components, such as paint layer 208 and surfacer layer 206.

In the depicted examples, a thickness of around 0.20 inches for depth 212 is desirable. Typical dielectric thicknesses are from around 0.002 to 0.018 inches. The different thicknesses depend on the particular color used for paint layer 208 as well as the part on which paint layer 208 is applied. In these illustrative embodiments, depth 212 is around 0.2 inches. An example of a larger depth for depth 212 is 0.42 inches. This type of thickness in depth 212 is typically seen after years of service in which additional coats of paint are applied to paint layer 208, thereby increasing the thickness of the dielectric layer.

The different advantageous embodiments recognize that in using an eddy current system to measure depths of wires and overlap width in an integrated wire fabric component, it is currently not possible to distinguish between the overlap area and a single thickness of an integrated wire fabric used on a component. The different advantageous embodiments provide a method and apparatus for nondestructive inspection of an interwoven wire fabric component.

Further, the different advantageous embodiments recognize that when the magnetic field generated by the current probe is too small, only individual wires are sensed. Also, if the magnetic field is too small, the gaps between the wires are sensed and read as an infinite depth of wire. Further, moving a probe with a small field only provides noise as the field rises over the wires and then drops again. The different advantageous embodiments also recognize that if a magnetic field generated by an eddy current probe is too large, the probe is unable to sense the presence of the wire because of comparatively large volume of electrically conductive graphite that is present in these types of materials.

The different advantageous embodiments provide a method and apparatus for nondestructive inspection of interwoven wire fabric components. The apparatus comprises a probe, a power source, and a display system. The probe is capable of creating a magnetic field for a plurality of wires in an interwoven wire fabric component such that disturbances of the magnetic field caused by the plurality of wires can be detected. The power is a source connected to the probe and is capable of sending an alternating current through the probe to generate the magnetic field for the wire. The display system is connected to the probe and is capable of displaying results from detecting the magnetic field and disturbances of the magnetic field.

In one advantageous embodiment, a system for nondestructive inspection of an interwoven wire fabric component has an arm that is capable of being moved over the interwoven wire fabric component. A probe connected to the scanner arm is capable of creating a magnetic field for a plurality of wires in an interwoven wire fabric component, such that disturbances of the magnetic field caused by the plurality of wires in response to the magnetic field can be detected. The scanner is present in this system and is capable of moving the scanner arm over the interwoven fabric component. A computer is present in the system and is capable of controlling the scanner to move the scanner arm and capable of receiving signals from the probe, wherein the computer generates results from the signals and presents the results on a display in the data processing system.

In another advantageous embodiment, a method for nondestructive inspection on an interwoven wire fabric component is provided. An alternating current at a frequency is sent though a probe coil having a number of coils, a diameter for the number of coils, and a diameter for a wire in the number of coils to generate a first magnetic field that generates a response in a selected number of wires in the interwoven wire fabric component. The probe coil is positioned in a location relative to the interwoven wire fabric component to cause the selected number of wires in the interwoven wire fabric component to generate a second magnetic field. Changes in the first magnetic field in response to the second magnetic field are detected.

The different illustrative embodiments also include a probe design that may be employed to measure the overlap width of a repair in which an interwoven wire fabric patch is present over an interwoven wire fabric component, such as a fuselage. Further, this probe also provides the ability to measure the thickness of a dielectric over the phosphor-bronze wires located in the interwoven wire fabric. In these examples, the dielectric includes, for example, paint, surfacer, and/or sealant thickness. Of course, other materials may be present in this dielectric depending on the implementation.

Figure 3:
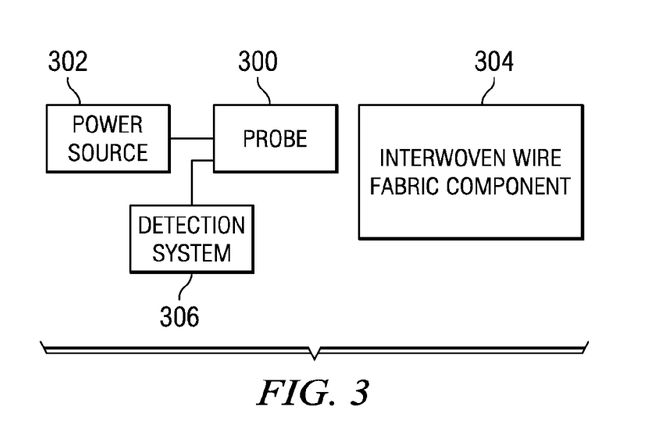
FIG. 3 is a diagram illustrating an apparatus for nondestructive inspection of an interwoven wire fabric component in accordance with an advantageous embodiment.

Turning now to FIG. 3, a diagram illustrating an apparatus for nondestructive inspection of an interwoven wire fabric component is depicted in accordance with an advantageous embodiment. In this example, probe 300 is connected to power source 302. Power source 302 generates an alternating current at a frequency that causes probe 300 to generate a magnetic field. This magnetic field may cause an eddy current within a selected number of wires within interwoven wire fabric component 304.

Probe 300 is designed and/or operated such that the selected number of wires provides a response that causes a disturbance in the magnetic field. The size of the magnetic field generated by probe 300 is selected to obtain a response from the selected number of wires. In these examples, the number of wires selected is such that the signal or data returned from probe 300 can be used to identify a depth of the selected wires and/or to identify an overlap of wires within interwoven wire fabric component 304.

The changes in the first magnetic field generated by probe 300, occurring in response to the second magnetic field, are detected and used to generate results. In other words, the second magnetic field causes a disturbance or change in the first magnetic field that may be quantified. In these examples, the disturbance or change is detected through a change in the inductive reactance for probe 300.

These results may be, for example, a depth of the selected number of wires from the surface of interwoven wire fabric component 304, or an amount of overlap width between wires in a patch to interwoven wire fabric component 304 and wires in the original portion of interwoven wire fabric component 304.

The disturbances in the first magnetic field in probe 300 are detected by detection system 306. In these examples, detection system 306 includes circuitry to detect the changes in the magnetic field generated by the flow of an alternating current through probe 300. The changes detected are changes in the inductive reactance in probe 300. Detection system 306 may include a display to present the changes in inductive reactance from disturbances to the magnetic field such that a user may see these changes. The changes in inductive reactance may occur as a user moves probe 300 over different sections of interwoven wire fabric component 304.

In this particular example, probe 300 is a hand held unit that is moveable by a person performing inspections. Detection system 306 may be a simple component or device that presents changes in the inductive reactance detected in probe 300. In this type of implementation, both power source 302 and detection system 306 may be located in the same box or unit. Alternatively, detection system 306 may be more complex and take the form of a computer that may record and store, as well as present data generated by probe 300.

Figure 4:
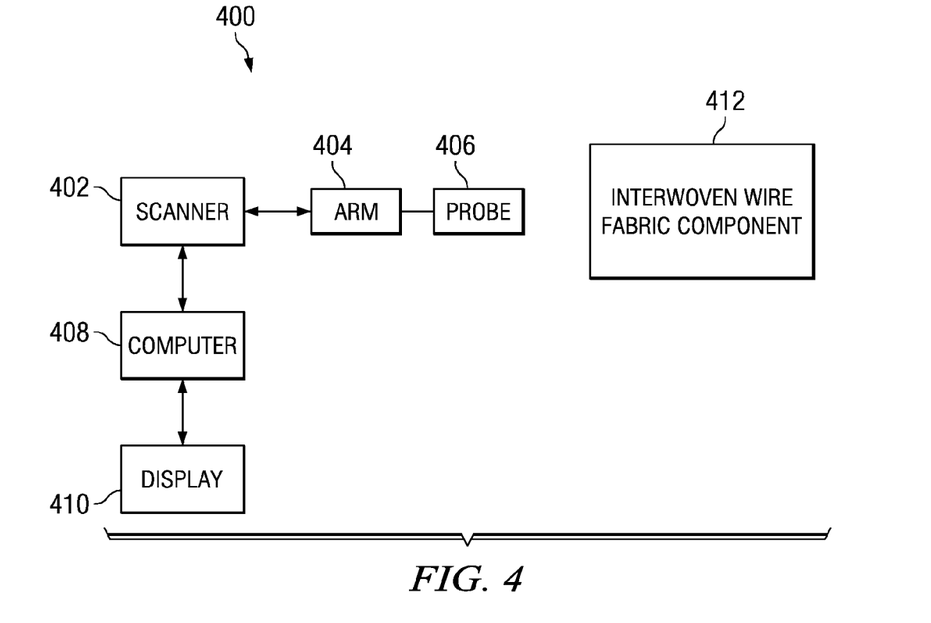
FIG. 4 is a diagram illustrating a scanning apparatus for nondestructive inspection of an interwoven wire fabric component in accordance with an advantageous embodiment.

Turning now to FIG. 4, a diagram illustrating a scanning apparatus for nondestructive inspection of an interwoven wire fabric component is depicted in accordance with an advantageous embodiment. In this example, system 400 includes scanner 402, arm 404, probe 406, computer 408, and display 410. These components in system 400 are used to provide nondestructive inspection of interwoven wire fabric component 412.

In these examples, probe 406 is mounted on or connected to arm 404. Arm 404 may be moved by scanner 402 over different sections of interwoven wire fabric component 412. Further, scanner 402 also provides a power source for probe 406. In these examples, the power source sends an alternating electric current through probe 406 at a frequency that causes probe 406 to generate a magnetic field. This field grows and collapses as the current alternates.

The magnetic field generated by probe 406 causes eddy currents within wires within interwoven wire fabric component 412. These eddy currents result in magnetic field being generated in those wires within interwoven wire fabric component 412. The magnetic fields generated in these wires cause disturbances or changes in the magnetic field generated by probe 406, as probe 406 moves along different sections of interwoven wire fabric component 412.

Computer 408, in these examples, receives the data or signals received from probe 406. The data or signals are generated by disturbances to the magnetic field being generated by probe 406 in response to magnetic fields generated within interwoven wire fabric component 412.

Further, computer 408 also generates instructions to direct movement of arm 404 by scanner 402 over different sections of interwoven wire fabric component 412. The results of scanning different sections of interwoven wire fabric component 412 may be displayed in display 410. This display may be presented as a color coded display, in which different magnetic field levels are displayed in different colors.

In this manner, a user may see the different wires present as well as an overlap in wires. Further, by displaying the data in different colors, depth information may be conveyed through colors. Further, display 410 also may display the inductive reactance of probe 406 as the scanning occurs while probe 406 is moved over interwoven wire fabric component 412 in these examples.

Probe 300 in FIG. 3 and probe 406 in FIG. 4 are designed or configured to generate the magnetic fields having a selected size. In these examples, the size of the magnetic field generated by these probes may be configured or selected based on a number of different parameters. Examples of parameters that may be selected include, a frequency of an alternating current, the probe coil in the probe, the number of coils, a diameter for the number of coils, and/or a diameter for the wire in the probe coil to generate a first magnetic field to generate a response in a selected number of wires in the interwoven wire fabric component. Further, in the depicted examples, probes 300 and 406 are unshielded. These parameters and other parameters also may be used to select or generate a particular shape for the magnetic field in addition to setting the size of the magnetic field generated by probes 300 in FIG. 3 and 406 in FIG. 4.

Figure 5:
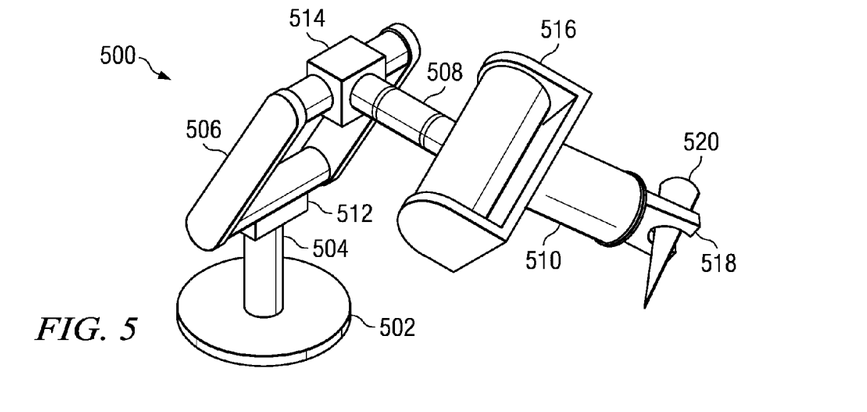
FIG. 5 is a diagram of a scanner arm in accordance with an advantageous embodiment.

Turning now to FIG. 5, a diagram of a scanner arm is depicted in accordance with an advantageous embodiment. In this example, scanner arm 500 is an example of one implementation of scanner arm 404 in FIG. 4. In this example, scanner arm 500 includes base 502. Support rod 504 is attached to base 502. Scanner arm 500 also includes support member 506, rod 508, and rod 510. These components are connected to each other by rotatary joints 512, 514, and 516. Rod 510 includes clamp 518, which holds probe 520. Probe 520 is an example of a probe, such as probe 300 in FIG. 3 or probe 406 in FIG. 4. These different components form an articulated arm for scanner arm 500 that can move probe 520 in three dimensions, along the X-axis, the Y-axis, and the Z-axis.

Scanner arm 500 includes motors for moving these components and circuits to receive commands directing the movement. These components may be controlled by commands from a device, such as computer 408 in FIG. 4. The particular depiction of scanner arm 500 is for purposes of illustration and not meant to limit the architecture or design that may be used to implement scanner arm 500.

Figure 6:
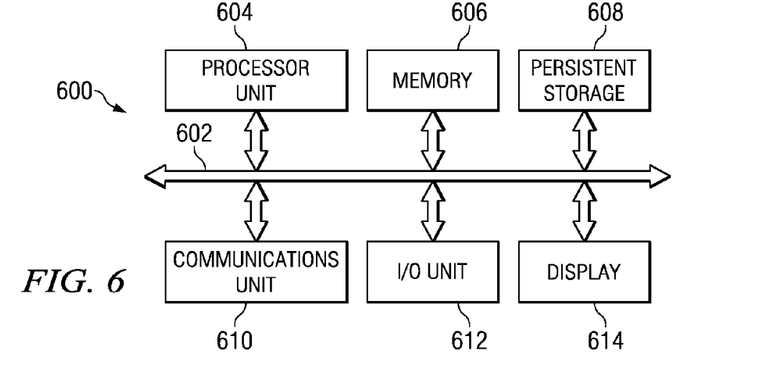
FIG. 6 is a diagram of a data processing system in accordance with an illustrative embodiment of the present invention.

Turning now to FIG. 6, a diagram of a data processing system is depicted in accordance with an illustrative embodiment of the present invention. In this illustrative example, data processing system 600 includes communications fabric 602, which provides communication between processor unit 604, memory 606, persistent storage 608, communications unit 610, input/output (I/O) unit 612, and display 614.

Processor unit 604 serves to execute instructions for software that may be loaded into memory 606. Processor unit 604 may be a set of one or more processors or may be a multiprocessor core, depending on the particular implementation. Further, processor unit 604 may be implemented using one or more heterogeneous processor systems in which a main processor is present with secondary processors on a single chip. Memory 606, in these examples, may be, for example, a random access memory. Persistent storage 608 may take various forms depending on the particular implementation. For example, persistent storage 608 may be, for example, a hard drive, a flash memory, a rewritable optical disk, a rewritable magnetic tape, or some combination of the above.

Communications unit 610, in these examples, provides for communications with other data processing systems or devices. In these examples, communications unit 610 is a network interface card. I/O unit 612 allows for input and output of data with other devices that may be connected to data processing system 600. For example, I/O unit 612 may provide a connection for user input though a keyboard and mouse. Further, I/O unit 612 may send output to a printer. Display 614 provides a mechanism to display information to a user.

Instructions for the operating system and applications or programs are located on persistent storage 608. These instructions may be loaded into memory 606 for execution by processor unit 604. The processes of the different embodiments may be performed by processor unit 604 using computer implemented instructions, which may be located in a memory, such as memory 606.

Figure 7:
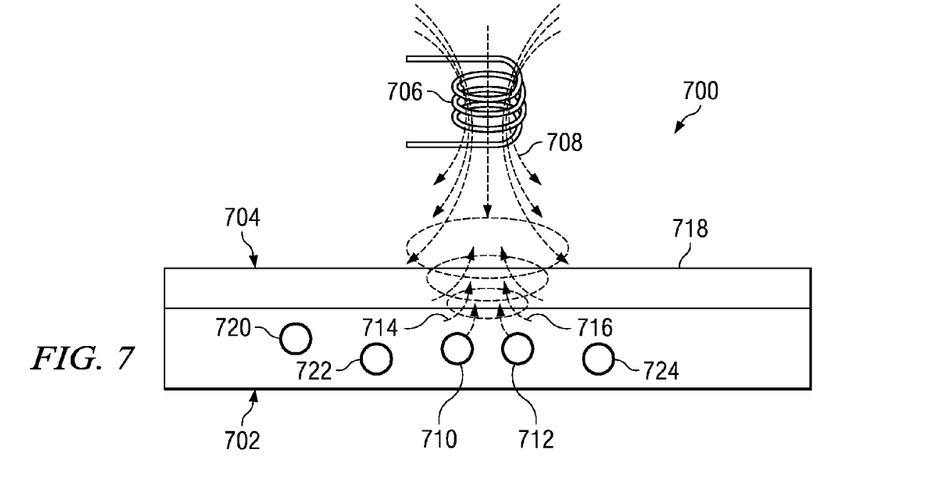
FIG. 7 is a diagram illustrating the use of a probe to detect wires in an interwoven wire fabric component in accordance with an advantageous embodiment.

With reference next to FIG. 7, a diagram illustrating the use of a probe to detect wires in an interwoven wire fabric component is depicted in accordance with an advantageous embodiment. In this example, interwoven wire fabric component 700 includes interwoven wire fabric layer 702 and dielectric layer 704. Probe 706 receives an alternating current at a selected frequency that generates magnetic field 708. Magnetic field 708 is generated such that the movement of probe 706 over wires, such as wires 710 and 712 will generate a disturbance in magnetic field 708 that can be detected.

More specifically, magnetic field 708 creates electrical currents in wires 710 and 712. These currents are referred to as eddy currents. These currents generate magnetic fields 714 and 716 in response. Magnetic fields 714 and 716 create a disturbance in magnetic field 708. This disturbance to magnetic field 708 may be detected using a measurement circuit connected to probe 706. These changes are detected and used to identify the depth of wires 710 and 712 below surface 718 of interwoven wire fabric component 700. The disturbance is detected in the change in the inductive reactance in probe 706, in these examples.

Reactance, denoted X, is a form of opposition that electronic components exhibit to the passage of alternating current because of capacitance or inductance. When alternating current passes through a component that contains reactance, energy is alternately stored in, and released from, a magnetic field or an electric field. In the case of a magnetic field, the reactance is inductive.

As described above, the design of probe 706 is such that only a selected number of wires are affected by magnetic field 708. In this example, the selected number of wires is two wires, wires 710 and 712. In this illustrative example, wires 720, 722, and 724 do not generate a response due to the size and configuration of magnetic field 708. In this example, the magnetic field is shown to generate a response into wires within interwoven wire fabric layer 702.

In particular, magnetic field 708 is generated in a manner to match the spacing between two wires in interwoven wire fabric layer 702. Of course, the magnetic field may be adjusted to encompass more wires or less wires depending on the particular implementation. The number of wires is selected such that the presence of individual wires within interwoven wire fabric layer 702 may be detected.

Figure 8:
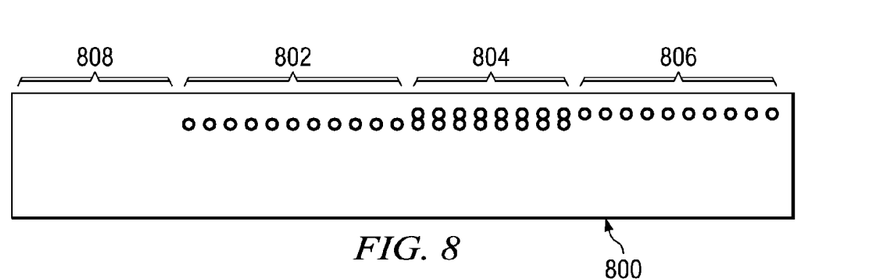
FIG. 8 is a diagram illustrating a cross-section of a wire fabric and overlap of fabric that generate responses to a probe moved over the component in accordance with an advantageous embodiment.

With reference to FIG. 8, a diagram illustrating a cross-section of a wire fabric and overlap of fabric that generate responses to a probe moved over the component is depicted in accordance with an advantageous embodiment. In this particular example, interwoven wire fabric component 800 is shown as a cross-section.

Section 802 contains wires for an original portion of interwoven wire fabric component 800. Section 804 contains wires that overlap with each other. The overlap of wires in this section occurs from a patch being placed into interwoven wire fabric component 800 as part of a repair. Section 806 contains wires only from the patch. Section 808 contains no wires in this example.

Figure 9:
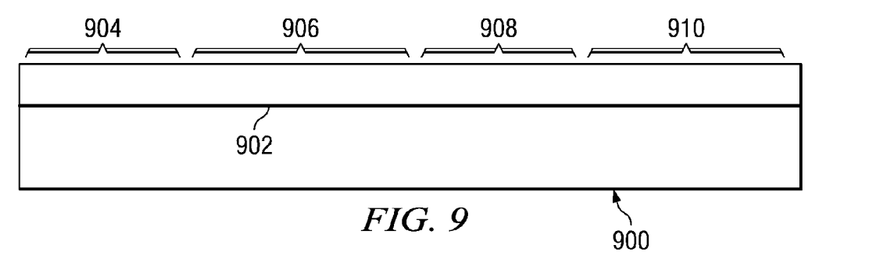
FIG. 9 is a response from a probe having a field that is too large in accordance with an advantageous embodiment.

Turning now to FIG. 9, a response from a probe having a field that is too large is depicted in accordance with an advantageous embodiment. In FIG. 9, graph 900 contains line 902 which represents a signal generated by a probe as the probe moves across interwoven wire fabric component 800 in FIG. 8. In these examples, the signal is for an inductive reactance in the probe.

In this example, the X-axis for graph 900 represents different locations across interwoven wire fabric component 800 in FIG. 8. The Y-axis, in these examples, represent values for inductive reactance measured for the probe, as the probe moves across interwoven wire fabric component 800 in FIG. 8. In these examples, sections 904, 906, 908, and 910 correspond to sections 808, 802, 804, and 806 in FIG. 8, respectively. Line 902 is a straight line because the field is too large. As a result, the probe is unable to provide data to distinguish between the presence or absence of wires within interwoven wire fabric component 800 in FIG. 8 and is sensing the general reactance produced by the skin cross-section, including the substrate.

Figure 10:
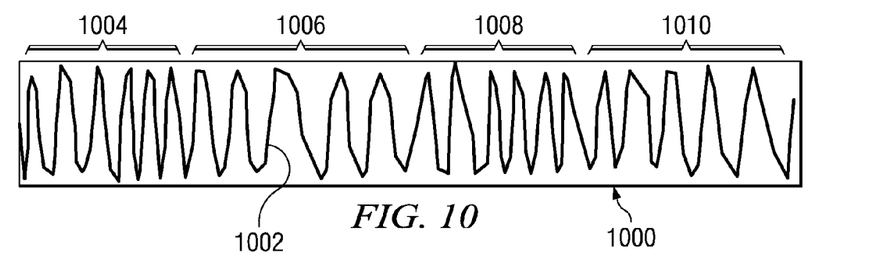
FIG. 10 is a diagram illustrating a probe response when the probe field is too small in accordance with an advantageous embodiment.

In FIG. 10, a diagram illustrating a probe response when the probe field is too small is depicted in accordance with an advantageous embodiment. In this example, graph 1000 contains line 1002 which represents a signal detected from a probe moving over interwoven wire fabric component 800 in FIG. 8.

The X-axis of graph 1000 represents different locations across interwoven wire fabric component 800 in FIG. 8. The Y-axis in graph 1000 represents values for inductive reactance measured or detected for the probe as it moves along different positions or locations for interwoven wire fabric component 800 in FIG. 8. In these examples, the value for different locations is a measurement of inductive reactance for the probe. Sections 1004, 1006, 1008, and 1010 correspond to sections 808, 802, 804, and 806 in FIG. 8, respectively.

In this example, the signal provides noise and is unable to provide any indication of the presence or absence of wires within interwoven wire fabric component 800 in FIG. 8 in the corresponding locations.

Figure 11:
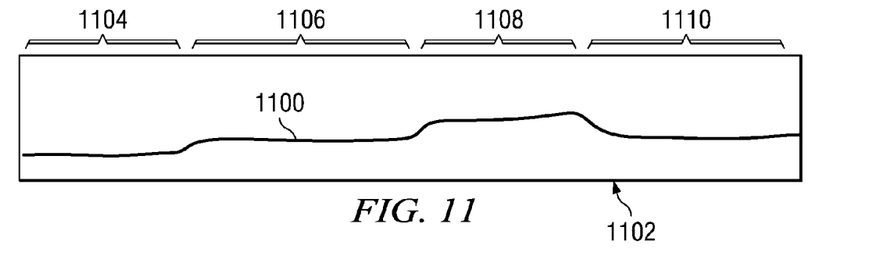
FIG. 11 is a diagram illustrating a probe response with a correct magnetic field size in accordance with an advantageous embodiment.

Turning now to FIG. 11, a diagram illustrating a probe response with a correct magnetic field size is depicted in accordance with an advantageous embodiment. In this particular example, the magnetic field generated by the probe is of a size that provides for an ability to distinguish or identify when wires are present, the depth of the wires as well as when wires between a patch and original portion of an interwoven wire fabric component overlap.

The X-axis represents different positions or locations across interwoven wire fabric component 800 in FIG. 8. The Y-axis represents the inductive reactance measured for the probe. In this example, line 1100 within graph 1102 represents inductive reactance, generated by a probe moving over interwoven wire fabric component 800 in FIG. 8. Line 1100 provides a user an ability to identify when a wire is present in an interwoven wire fabric component.

Section 1104 shows a signal corresponding to section 808 in FIG. 8. As can be seen, the signal is lower when wire is absent. Section 1106 corresponds to section 802 in FIG. 8. This signal indicates that a single layer of wires is present. Section 1108 of signal 1100 indicates an overlap between wires that corresponds to section 804 in FIG. 8. Section 1110 provides a signal that corresponds to section 806 in FIG. 8. As can be seen, in these examples, an identification of wires may be made within interwoven wire fabric component 800 in FIG. 8. Further, the depth or the distance of the wires from the surface may be identified through the signals.

Figure 12:
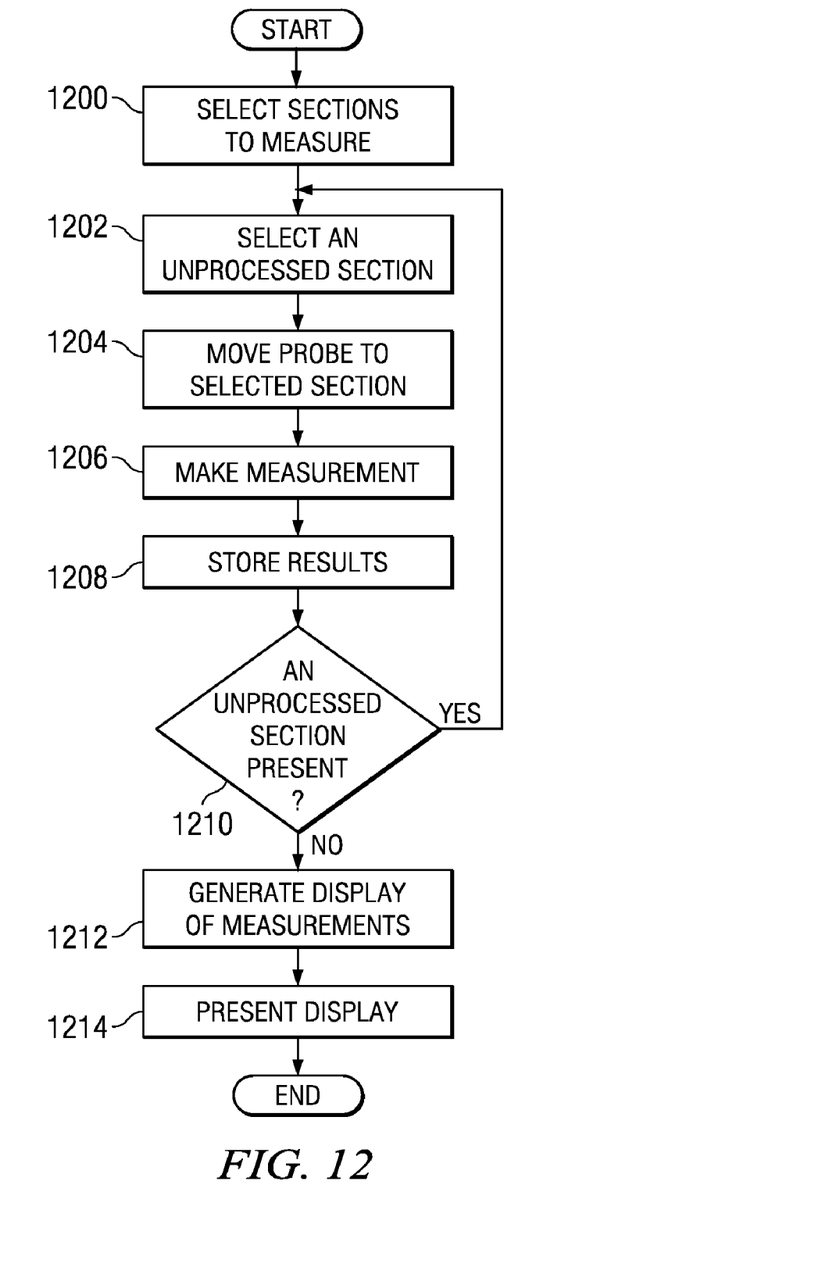
FIG. 12 is a flowchart of a process for nondestructive inspection of a component containing an interwoven wire fabric layer in accordance with an advantageous embodiment.

Turning now to FIG. 12, a flowchart of a process for nondestructive inspection of a component containing an interwoven wire fabric layer is depicted in accordance with an advantageous embodiment. The process illustrated in FIG. 12 may be implemented in a scanning system, such as system 400 in FIG. 4. In particular, the different operations may be implemented in a computer, such as computer 408 in FIG. 4.

The process begins by selecting sections of a component to be measured (operation 1200). Thereafter, an unprocessed selection within the selected sections is selected for processing (operation 1202). Next, the probe is moved to the selected section (operation 1204). In this example, operation 1204 is accomplished by sending instructions to a scanner to move the arm holding the probe to the appropriate section. A measurement is then made (operation 1206).

Thereafter, the results of the measurement are stored (operation 1208). Next, a determination is made as to whether an unprocessed section is present (operation 1210). If an unprocessed section is present, the process returns to operation 1202 as described above. Otherwise, a display of measurements is generated (operation 1212).

Then, the display of the measurement is presented (operation 1214) with the process terminating thereafter. In operation 1212, the displayed measurements may be a two dimensional representation of the sections that were probed or measured. The values for the measurements may be represented using color coding. For example, measurements identifying a wire may be presented in one color. The particular intensity or shade of the color may be varied for the depth of the dielectric along those sections. Further, an overlap width between the original portion of the interwoven wire fabric component and a repaired or patched portion on the interwoven wire fabric component also may be identified using a different color. The amount of overlap, also referred to as the overlap width, may be identified based on the width or sections that this color is presented.

The flowcharts and block diagrams in the different depicted embodiments illustrate the architecture, functionality, and operation of some possible implementations of apparatus, methods and computer program products. In this regard, each block in the flowchart or block diagrams may represent a module, segment, or portion of code, which comprises one or more executable instructions for implementing the specified function or functions. In some alternative implementations, the function or functions noted in the block may occur out of the order noted in the figures. For example, in some cases, two blocks shown in succession may be executed substantially concurrently, or the blocks may sometimes be executed in the reverse order, depending upon the functionality involved.

Thus, the different advantageous embodiments provide a method and apparatus for nondestructive inspection of an interwoven wire fabric component. The apparatus comprises a probe, a power source, and a display system. The probe is capable of creating a magnetic field for a plurality of wires in an interwoven wire fabric component such that disturbances of the magnetic field caused by the plurality of wires can be detected. The power source connected to the probe is capable of sending an alternating current through the probe to generate the magnetic field for the wire. The display system is connected to the probe and is capable of displaying results from detecting the magnetic field and disturbances of the magnetic field.

In one advantageous embodiment, a system for nondestructive inspection of an interwoven wire fabric component comprises a scanner arm, a probe, a scanner, and a computer. The scanner arm is capable of being moved over the interwoven wire fabric component. The probe connected to the scanner arm is capable of creating a magnetic field for a plurality of wires in an interwoven wire fabric component such that disturbances of the magnetic field caused by the plurality of wires in response to the magnetic field can be detected. The scanner is capable of moving the scanner arm over the interwoven fabric component. The computer is capable of controlling the scanner to move the scanner arm and capable of receiving signals from the probe, wherein the computer generates results from the signals and presents the results on a display in the data processing system.

In another advantageous embodiment, a method for nondestructive inspection on an interwoven wire fabric component is present. An alternating current at a frequency is sent though a probe coil having a number of coils, a diameter for the number of coils, and a diameter for a wire in the number of coils to generate a first magnetic field that generates a response in a selected number of wires in the interwoven wire fabric component. The probe coil is position in a location relative to the interwoven wire fabric component to cause the selected number of wires in the interwoven wire fabric component to generate a second magnetic field. Changes in the first magnetic field in response to the second magnetic field are detected.

With these and other advantageous embodiments, inspections of interwoven wire fabric components can be made in a nondestructive manner. The different embodiments allow for identifying depth of wires in interwoven wire fabric components. The embodiments also may be used to identify an amount of overlap between wires in a patch and the wires in the original portions of interwoven wire fabric components.

The description of the different advantageous embodiments has been presented for purposes of illustration and description, and is not intended to be exhaustive or limited to the invention in the form disclosed. Many modifications and variations will be apparent to those of ordinary skill in the art. Further, different advantageous embodiments may provide different advantages as compared to other advantageous embodiments. The embodiment or embodiments selected are chosen and described in order to best explain the principles of the invention, the practical application, and to enable others of ordinary skill in the art to understand the invention for various embodiments with various modifications as are suited to the particular use contemplated.

What is claimed is:

1. An apparatus for nondestructive inspection of an interwoven wire fabric component, the apparatus comprising:
   a probe configured to generate a magnetic field for a plurality of wires in an interwoven wire fabric component such that disturbances in the magnetic field caused by the plurality of wires can be detected;
   a power source connected to the probe and configured to send an alternating current through the probe to generate the magnetic field for the plurality of wires; and
   a display system connected to the probe and configured to display results from detecting the magnetic field and disturbances of the magnetic field, wherein the results comprise an amount of overlap between wires in the plurality of wires from a patch to the interwoven wire fabric component that overlap other wires in the plurality of wires from an original portion of the interwoven wire fabric component.

2. The apparatus of claim 1, wherein the probe comprises a number of coils of a wire, a diameter for the number of coils of the wire, and a diameter of the wire, wherein the number coils of the wire, the diameter of the number of coils of the wire, and the diameter of the wire in the number of coils cause the creation of the magnetic field for a plurality of wires in an interwoven wire fabric component that can distinguish the plurality of wires from other wires in the interwoven wire fabric components such that disturbances of the magnetic field can be detected.

3. The apparatus of claim 1, wherein the results comprise a depth of the plurality of wires below a surface of the interwoven wire fabric component.

4. The apparatus of claim 1 further comprising:
   an arm connected to the probe; and
   a scanner connected to the arm, wherein the scanner moves the arm to move the probe over different sections of the interwoven wire fabric component.

5. The apparatus of claim 4, wherein the display system displays results from the different sections of the interwoven wire fabric component.

6. The apparatus of claim 5, wherein the results are depths of wires in the different sections of the interwoven wire fabric components and wherein the display system displays the depths using color coding.

7. The apparatus of claim 1, wherein the wire is comprised of a phosphor-bronze wire.

8. The apparatus of claim 1, wherein the interwoven wire fabric component is a section of a fuselage of an aircraft.

9. A system for nondestructive inspection of an interwoven wire fabric component, the system comprising:
   a scanner arm configured to move over the interwoven wire fabric component;
   a probe connected to the scanner arm, wherein the probe is configured to create a magnetic field for a plurality of wires in an interwoven wire fabric component such that disturbances of the magnetic field caused by the plurality of wires in response to the magnetic can be detected;
   a scanner configured to move the scanner arm over the interwoven fabric component; and
   a computer configured to control the scanner to move the scanner arm and configured to receive signals from the probe, wherein the computer generates results from the signals and presents the results on a display in the data processing system, wherein the results comprise an amount of overlap between wires in the plurality of wires from a patch to the interwoven wire fabric component that overlap other wires in the plurality of wires from an original portion of the interwoven wire fabric component.

10. The system of claim 9, wherein the probe comprises a number of coils of a wire, a diameter for the number of coils of the wire, and a diameter of the wire, wherein the number coils of the wire, the diameter of the number of coils of the wire, and the diameter of the wire in the number of coils cause the creation of the magnetic field for a plurality of wires in an interwoven wire fabric component that can distinguish the plurality of wires from other wires in the interwoven wire fabric components such that disturbances of the magnetic field can be detected.

11. The system of claim 9, wherein the results comprise a depth of the plurality of wires below a surface of the interwoven wire fabric component.

12. A method for nondestructive inspection on an interwoven wire fabric component, the method comprising:

sending an alternating current at a frequency through a probe coil having a number of coils, a diameter for the number of coils, and a diameter for a wire in the number of coils to generate a first magnetic field that generates a response in a selected number of wires in the interwoven wire fabric component;

positioning the probe coil in a location relative to the interwoven wire fabric component to cause the selected number of wires in the interwoven wire fabric component to generate a second magnetic field; and detecting changes in the first magnetic field in response to the second magnetic field.

13. The method of claim 12 further comprising:

moving the probe coil over a plurality of sections of the interwoven wire fabric component; and recording a set of measurements at each of the plurality of locations to form measured data.

14. The method of claim 13, wherein the measurements comprise a depth of wires below a surface of the interwoven wire fabric components and further comprising:

processing the measured data to identify a thickness of a dielectric layer at each section in the interwoven wire fabric component to form thickness data.

15. The method of claim 14 further comprising:

generating a display using the thickness data, wherein the display uses color coding to identify the thickness of a dielectric layer in each section.

16. The method of claim 13 further comprising:

processing the measured data to identify a presence of an overlap between wires in an original interwoven wire fabric in the interwoven wire fabric component and wires in a patch to the interwoven wire fabric component in each section of the interwoven wire fabric component to form overlap data.

17. The method of claim 13 further comprising:

generating a display using the overlap data, wherein the display identifies an amount of overlap between wires in an original portion of interwoven wire fabric in the interwoven wire fabric component and wires in a patch to the interwoven wire fabric component in each section of the interwoven wire fabric component.

* * * * *